US00PP22213P2

(12) United States Plant Patent
Hartman

(10) Patent No.: US PP22,213 P2
(45) Date of Patent: Oct. 25, 2011

(54) ***CALADIUM* PLANT NAMED 'BLUSHING BRIDE'**

(50) Latin Name: *Caladium×hortulanum*
Varietal Denomination: Blushing Bride

(76) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 12/804,002

(22) Filed: Jul. 12, 2010

(51) Int. Cl.
*A01H 5/00* (2006.01)

(52) U.S. Cl. ..... Plt./373
(58) Field of Classification Search ..... Plt./373
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Caladium* plant named 'Blushing Bride', characterized by its upright and mounding plant habit; intermediate plant size; uniform potted plant habit; vigorous and dense growth habit; fast growth rate; and lance-type greyed purple-colored leaves with dark green-colored margins and whitish-colored venation tinged with greyed purple.

4 Drawing Sheets

Botanical designation: *Caladium×hortulanum.*
Cultivar denomination: 'BLUSHING BRIDE'.

BACKGROUND OF THE INVENTION

The present invention relates to a new and distinct cultivar of *Caladium* plant, botanically known as *Caladium×hortulanum,* commercially referred to as a lance leaf-type *Caladium* and hereinafter referred to by the name 'Blushing Bride'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2002, in Lake Placid, Fla. of *Caladium×hortulanum* 'Pink Symphony', not patented, as the female, or seed, parent with *Caladium×hortulanum* 'Aaron', not patented, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2003.

Asexual reproduction of the new *Caladium* plant by tuber divisions in a controlled outdoor nursery environment in Lake Placid, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'Blushing Bride'. These characteristics in combination distinguish 'Blushing Bride' as a new and distinct *Caladium* plant:

1. Upright and mounding plant habit; intermediate plant size.
2. Uniform potted plant habit.

3. Vigorous and dense growth habit.
4. Fast growth rate.
5. Lance-type greyed purple-colored leaves with dark green-colored margins and whitish-colored venation tinged with greyed purple.

Plants of the new *Caladium* differ primarily from plants of the female parent, 'Pink Symphony', in the following characteristics:

1. Plants of the new *Caladium* are more compact than and not as upright as plants of 'Pink Symphony'.
2. Plants of the new *Caladium* grow faster than plants of 'Pink Symphony'.
3. Plants of the new *Caladium* and 'Pink Symphony' differ in leaf coloration as plants of 'Pink Symphony' have light pink to white-colored leaves with green-colored margins and green-colored venation.

Plants of the new *Caladium* differ primarily from plants of the male parent, 'Aaron', in the following characteristics:

1. Plants of the new *Caladium* are shorter than plants of 'Aaron'.
2. Plants of the new *Caladium* grow faster than plants of 'Aaron'.
3. Plants of the new *Caladium* and 'Aaron' differ in leaf coloration as plants of 'Aaron' have white-colored leaves with green-colored margins and white-colored venation.

Plants of the new *Caladium* can be compared to plants of 'Florida Sweetheart', disclosed in U.S. Plant Pat. No. 8,526. In side-by-side comparisons conducted in Lake Placid, Fla., plants of the new *Caladium* differed primarily from plants of 'Florida Sweetheart' in the following characteristics:

1. Plants of the new *Caladium* were taller and more upright than plants of 'Florida Sweetheart'.
2. Leaves of plants of the new *Caladium* were more elongate than and not as broad as leaves of plants of 'Florida Sweetheart'.
3. Plants of the new *Caladium* and 'Florida Sweetheart' differed in leaf coloration as plants of 'Florida Sweetheart' had light pink-colored leaves with white and green-colored margins and rose-colored venation.

4. Plants of the new *Caladium* and 'Florida Sweetheart' differed in spathe coloration as plants of 'Florida Sweetheart' had white to off-white-colored spathes.

Plants of the new *Caladium* can also be compared to plants of 'Thai Beauty', not patented. In side-by-side comparisons conducted in Lake Placid, Fla., plants of the new *Caladium* differed primarily from plants of 'Thai Beauty' in leaf coloration as plants of 'Thai Beauty' had pale pink to white-colored leaves with white to green-colored margins and venation.

BRIEF DESCRIPTION OF THE PHOTOGRAPHS

The accompanying photographs illustrate the overall appearance of the new *Caladium* plant. These photographs show the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Blushing Bride' grown in a 15-cm container in a shadehouse.

The photograph at the top of the second sheet is a top perspective view of typical plants of 'Blushing Bride' grown in an outdoor nursery.

The photograph at the bottom of the second sheet is a close-up view of typical freshly-dug tubers and roots of 'Blushing Bride'.

The photograph on the third sheet is a close-up view of a typical inflorescence of 'Blushing Bride'.

The photograph at the top of the fourth sheet is a side perspective view of typical potted plants of the male parent, 'Aaron' (left), 'Blushing Bride' (center) and the female parent, 'Pink Symphony' (right).

The photograph at the bottom of the fourth sheet is a side perspective view of typical potted plants of 'Thai Beauty' (left), 'Blushing Bride' (center) and 'Florida Sweetheart' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown in ground beds in an outdoor nursery in Zolfo Springs, Fla. during the late autumn and early winter. All plants were grown under conditions and practices which approximate those generally used in commercial shadehouse and outdoor nursery *Caladium* production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants had been growing in the shadehouse for ten weeks from planting tubers when the photographs and the detailed description were taken. Plants had been growing in the outdoor nursery for eight months from planting tuber divisions when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Blushing Bride'.

Parentage:

*Female, or seed, parent.*—*Caladium×hortulanum* 'Pink Symphony', not patented.

*Male, or pollen, parent.*—*Caladium×hortulanum* 'Aaron', not patented.

Propagation:

*Type.*—By tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate to round in shape. Height: About 3.4 cm. Diameter: About 4.3 cm. Texture: Thick and starchy; somewhat brittle. Color: Epidermis, close to 161D, 164D and 199D; interior, close to 200A to 200B. Root description: Dense, thick, fleshy contractile roots with few lateral branches; color, close to 155C.

Plant description:

*Plant type.*—Herbaceous perennial; suitable as a potted plant in containers 15-cm to 25-cm and suitable as a landscape plant in shaded areas.

*Plant and growth habit.*—Upright and mounding plant habit; intermediate plant size; inverted triangle; vigorous and dense growth habit; rapid growth rate; petioles and leaves arise from one or more growing points on tubers; petioles mostly upright and leaning outwardly with development.

*Plant height, from soil level to top of leaf plane, shadehouse-grown potted plants.*—About 20 cm to 26 cm.

*Plant height, from soil level to top of inflorescences, shadehouse-grown plants.*—About 26 cm.

*Plant diameter or spread, shadehouse-grown plants.*—About 40 cm to 44 cm.

*Number of clumps per plant, shadehouse-grown plants.*—About five to eight from tubers.

*Cataphylls, shadehouse-grown plants.*—Length: About 4.5 cm. Width: About 1.2 cm. Shape: Lanceolate. Apex: Acute. Base: Sheathing the stem. Color, inner and outer surfaces: Between 159C to 157B tinged with close to 148B; fine streaks and speckles, close to 147A; with development, color becoming closer to 200D.

Foliage description:

*Length, shadehouse-grown plants.*—About 13 cm to 20 cm.

*Width, shadehouse-grown plants* (*flattened*).—About 8 cm to 10.5 cm.

*Shape.*—Ovate.

*Apex.*—Acuminate to acute.

*Base.*—Sagittate to cordate.

*Margin.*—Entire with broad undulations.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Ground color of close to 158D, 155C or 146A with large intervenal areas close to 184B, 184C to 184D or close to 181C. Margins: Close to 147A and N189A; basal notch, close to 59A. Venation: Midrib, close to 155C with random flecks and streaks of close to 184D; primary veins, similar to lamina color and purple tinging. Developing leaves, lower surface: Center: Ground color of close to 155C tinged with close to 184C with random streaks and intervenal areas close to 184B or 184B to 184C. Margins: Close to 191A. Venation: Midrib, close to 147C to 147D tinged with close to N170D; primary veins, close to 147B to 147C or 147C. Fully expanded leaves, upper surface: Center: Intervenal areas of close to 185C to 185D or between 185D to 186D. Margins: Close to 147A and N189A; basal notch, close to 59A to 59B. Venation: Midrib, close to 156B; primary veins, close to 155C, close to 156B or close to 156B tinged with close to 184B to 184C. Fully expanded leaves, lower surface: Center: Intervenal areas of close to 184C to 184D. Margins: Close to 191A; basal notch, close to 59A to 59B. Venation: Midrib, close to 147C to 147D tinged with close to N170D; primary veins, close to 147C to 147D.

*Petiole.*—Aspect: Mostly erect, outwardly leaning and arching with development; flexible. Length, shadehouse-grown plants: About 16 to 19 cm. Diameter, distal, shadehouse-grown plants: About 4 mm. Diameter, proximal, shadehouse-grown plants: About 5 mm to 10 mm. Color, shadehouse-grown plants, distal: Close to 157A. Color, shadehouse-grown plants, proximal: Close to 159C tinged with close to 157B, 177D and 148B with fine streaks, close to 147A. Wing length, shadehouse-grown plants: About 2.5 cm to 3 cm. Wing diameter, shadehouse-grown plants: About 8 mm to 10 mm. Wing color, shadehouse-grown plants, outer and inner surfaces: Close to 159C and 157B tinged with close to 148B and with fine streaks and speckles, close to 147A.

Inflorescence description: Inflorescences observed on shadehouse-grown plants.

*Inflorescence arrangement.*—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop between female and male flower zones; near this area, the spathe constricts and surrounds and encloses the female flowers; spathe open and cupped around male flowers.

*Fragrance.*—None detected.

*Natural flowering season/longevity.*—Plants of the new *Caladium* typically flower during the spring or early summer in central Florida; flowers develop about nine to ten weeks after growth commences; inflorescences last about three days before fading; inflorescences persistent.

*Spathe.*—Length: About 7.7 cm; open length, about 4.8 cm and closed length, about 2.9 cm. Width, distal: About 1.9 cm. Width, proximal: About 1.8 cm. Width, at constriction: About 1.3 cm. Shape: Ovate. Apex: Acute. Base: Tapering to the peduncle. Margin: Entire. Texture, upper and lower surfaces: Smooth, glabrous. Color: Front surface: Upper two-thirds: Towards the apex, close to N155B mottled with close to 184B to 184D; towards the female zone, close to N155B, with development, color becoming closer to 199D and 200D. Lower one-third: Close to 148C with longitudinal streaks, close to 147B; towards the base, close to 148C tinged with close to 187A; with development, color becoming closer to 147C with longitudinal streaks, close to 148A to 148B, and areas of close to 155A. Rear surface: Upper two-thirds: Close to 158C tinged with close to 146C to 146D; towards the margins, close to N155B mottled with close to 184B to 184D. Lower one-third: Close to 147C with longitudinal streaks, close to 148A to 148B, and areas of close to 155A. Spadix: Length: About 5.3 cm. Length, male flower zone: About 2.6 cm. Length, female flower zone: About 1.8 cm. Length, sterile flower zone: About 9 mm. Diameter, male flower zone: About 8 mm. Diameter, female flower zone: About 9 mm. Diameter, sterile flower zone: About 5 mm. Shape: Columnar. Apex: Acute. Base: Obtuse. Aspect: Upright. Color, mature, male zone: Close to 159D. Color, mature, sterile zone: Close to 159D. Color, mature, female zone: Between 159A and 162C. Male flowers: Quantity per spadix: About 145. Shape: Obovate. Height: About 3 mm. Diameter: About 3 mm. Pollen amount: Moderate. Pollen color: Close to 11C. Female flowers: Quantity per spadix: About 120. Shape: Obovate. Height: About 3 mm. Diameter: About 1.5 mm. Stigma color: Close to 159D. Ovary color: Close to 155B. Scape: Length: About 15.5 cm. Diameter: About 5 mm. Strength: Sturdy; flexible. Aspect: Erect. Texture: Smooth, glabrous; glaucous. Color: Close to 148B to 148C with fine streaks/speckles, close to 147A; just below spathe, close to 146B. Seed and fruit: Seed and fruit development have not been observed on plants of the new *Caladium*.

Disease/pest resistance: Plants of the new *Caladium* have not been observed to be resistant to pathogens and pests common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Blushing Bride' as illustrated and described.

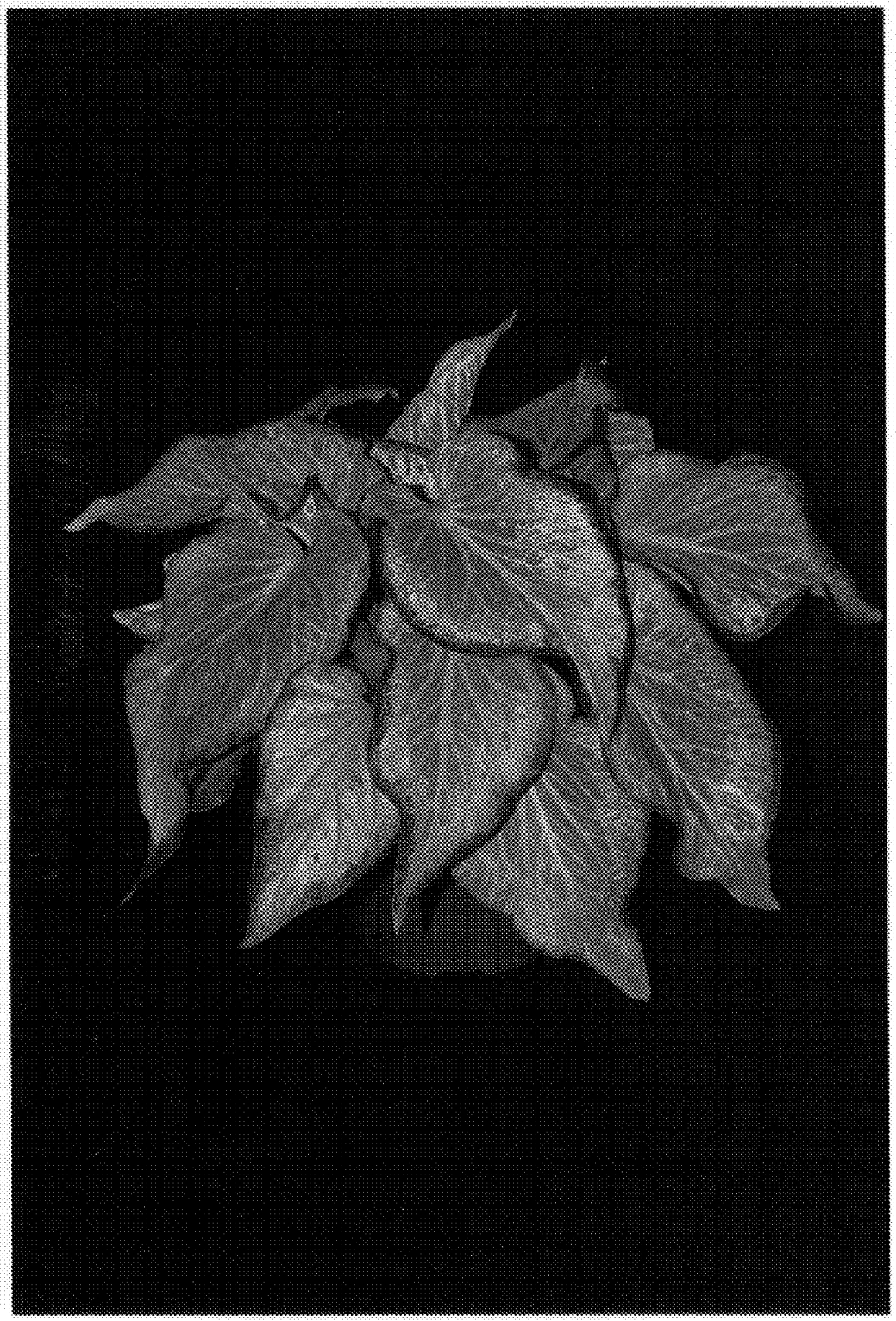

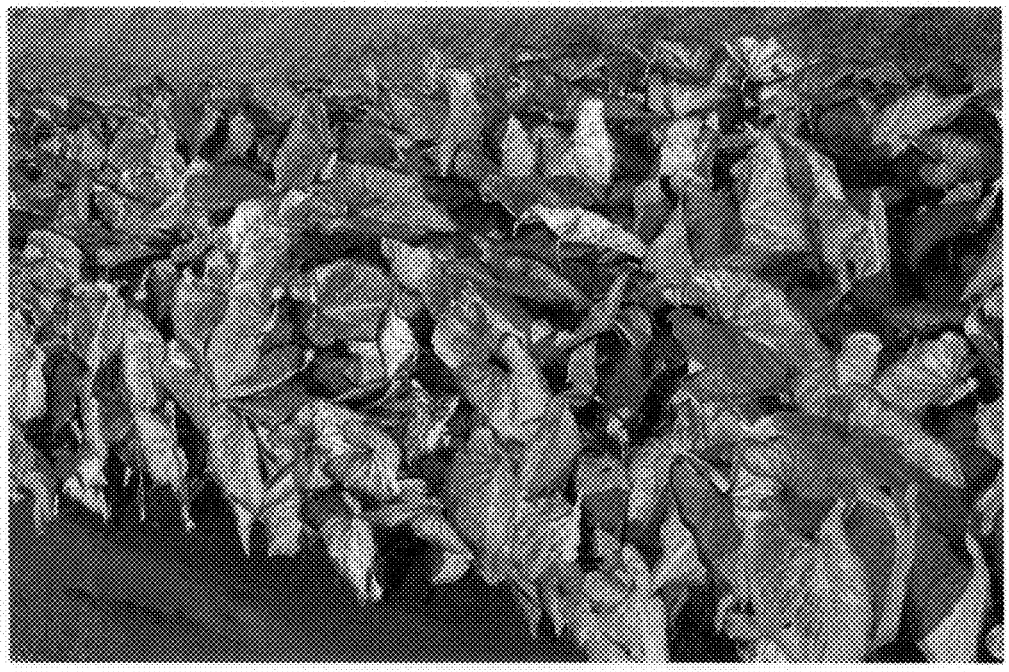
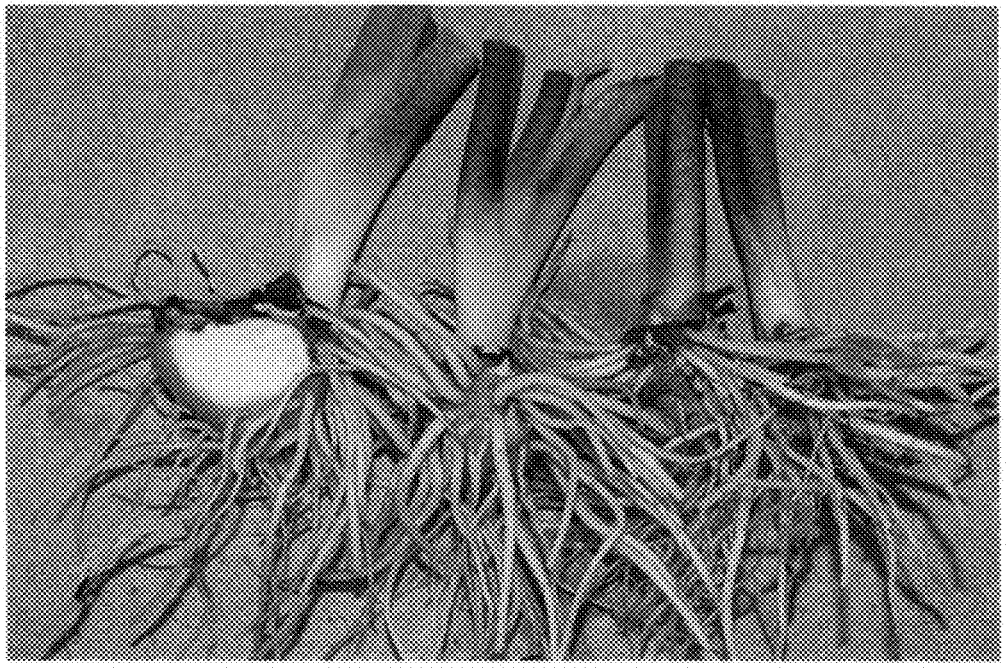

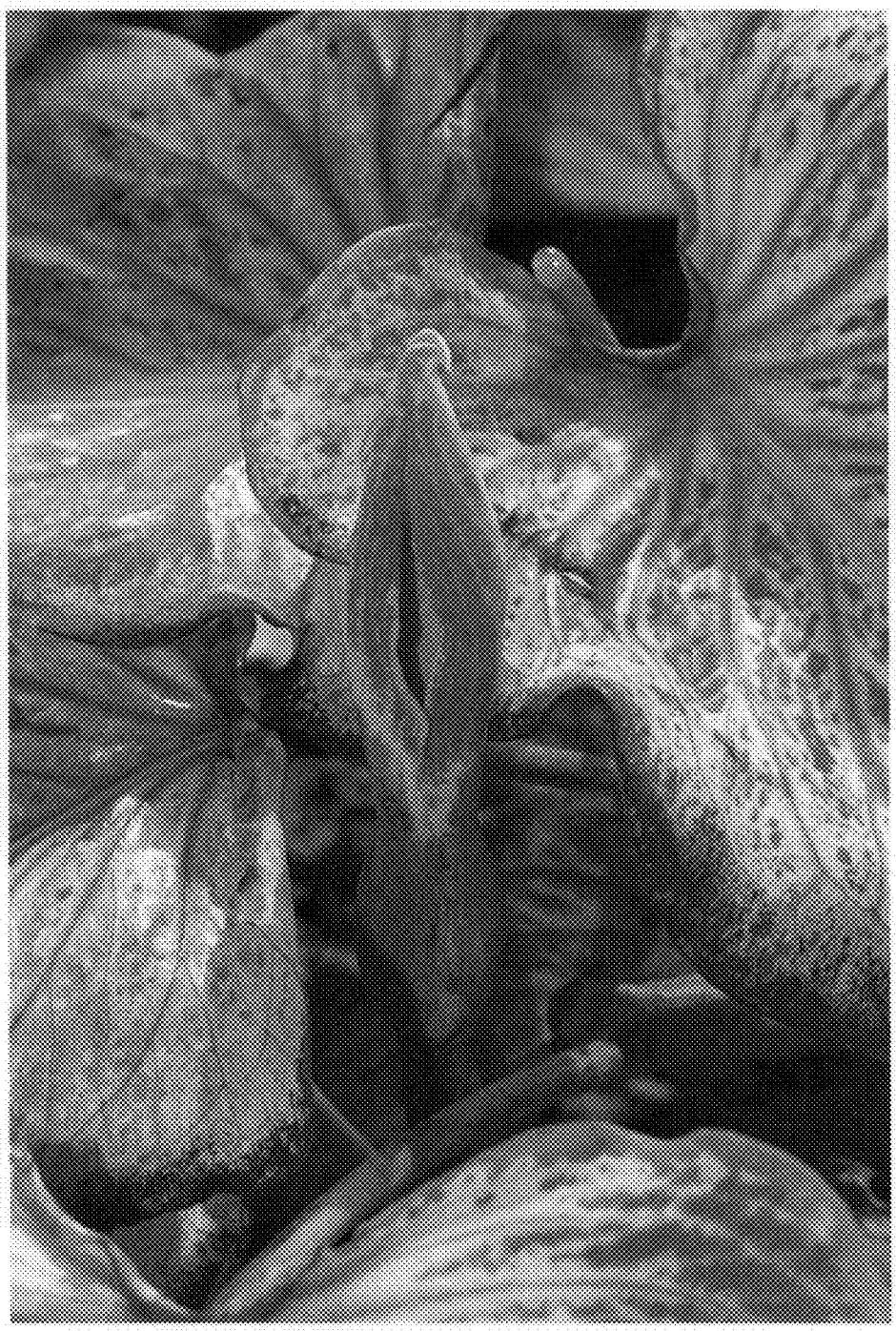

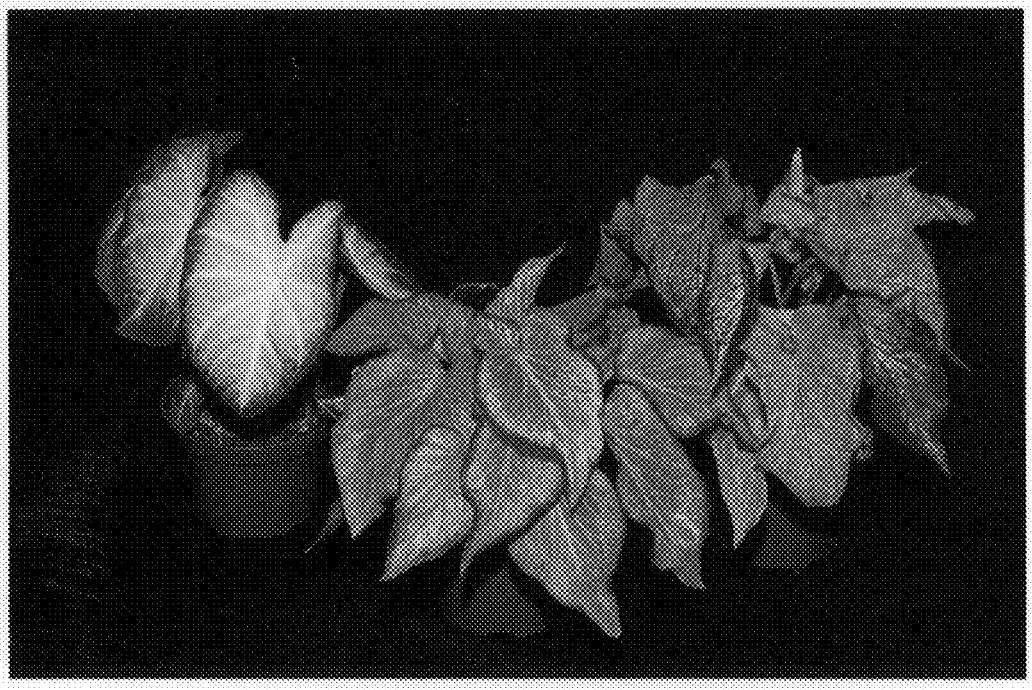
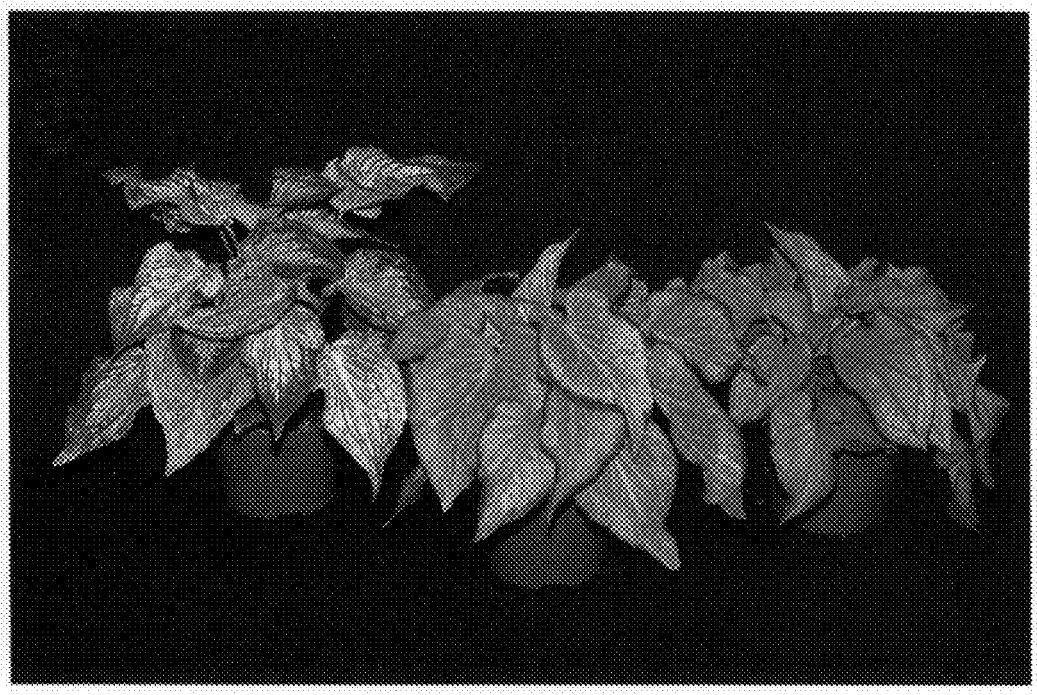

* * * * *